United States Patent
Chen et al.

(10) Patent No.: US 11,162,056 B2
(45) Date of Patent: *Nov. 2, 2021

(54) ENCAPSULATION METHOD

(71) Applicant: Dow Global Technologies LLC, Midland, MI (US)

(72) Inventors: Xue Chen, Manvel, TX (US); Xin Jin, Berwyn, PA (US); An Kaga, Rosharon, TX (US)

(73) Assignee: DOW GLOBAL TECHNOLOGIES LLC, Midland, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 16/632,912

(22) PCT Filed: Jul. 10, 2018

(86) PCT No.: PCT/US2018/041369
§ 371 (c)(1),
(2) Date: Jan. 22, 2020

(87) PCT Pub. No.: WO2019/027632
PCT Pub. Date: Feb. 7, 2019

(65) Prior Publication Data
US 2020/0165546 A1 May 28, 2020

Related U.S. Application Data

(60) Provisional application No. 62/539,169, filed on Jul. 31, 2017.

(51) Int. Cl.
| | | |
|---|---|---|
| *C11D 3/39* | (2006.01) | |
| *A01N 25/28* | (2006.01) | |
| *A61K 8/11* | (2006.01) | |
| *A61K 8/37* | (2006.01) | |
| *A61K 9/48* | (2006.01) | |
| *C11D 17/00* | (2006.01) | |

(52) U.S. Cl.
CPC .......... *C11D 3/3935* (2013.01); *A01N 25/28* (2013.01); *A61K 8/11* (2013.01); *A61K 8/37* (2013.01); *A61K 9/4833* (2013.01); *C11D 3/3917* (2013.01); *C11D 17/0039* (2013.01)

(58) Field of Classification Search
CPC ....... C01D 3/3917; C01D 3/3935; A61K 8/37
See application file for complete search history.

(56) References Cited

U.S. PATENT DOCUMENTS

| | | | | |
|---|---|---|---|---|
| 4,957,983 A | * | 9/1990 | Hawrylko | ............... C08F 14/06 526/200 |
| 5,347,043 A | * | 9/1994 | Sabahi | .................. C07C 67/343 560/190 |
| 2003/0073757 A1 | * | 4/2003 | Moy | .................... C08F 22/1006 522/176 |
| 2006/0078742 A1 | * | 4/2006 | Kauffman | ............... C08L 65/00 428/411.1 |
| 2006/0084715 A1 | | 4/2006 | Fechter et al. | |
| 2007/0173602 A1 | * | 7/2007 | Brinkman | ......... C08F 222/1006 524/592 |
| 2011/0251338 A1 | * | 10/2011 | Kim | ..................... C09D 133/14 524/559 |
| 2013/0287844 A1 | * | 10/2013 | Taranta | ................... C08L 75/02 424/455 |

FOREIGN PATENT DOCUMENTS

| | | | | |
|---|---|---|---|---|
| WO | 1998016621 | | 4/1998 | |
| WO | 2008141187 | | 11/2008 | |
| WO | WO-2017040501 A | * | 3/2017 | ......... C11D 11/0017 |
| WO | WO-2017134308 A1 | * | 8/2017 | ............. A01N 47/24 |

OTHER PUBLICATIONS

PCT/US2018/041369, International Search Report and Written Opinion dated Oct. 8, 2018.
PCT/US2018/041369, International Preliminary Report on Patentability dated Feb. 4, 2020.

* cited by examiner

*Primary Examiner* — Isaac Shomer

(57) ABSTRACT

A method of encapsulating an active comprising preparing a first mixture comprising the active, a compound that functions as a Michael donor, and a compound that functions as a Michael acceptor, preparing a second mixture comprising water and an emulsifier; preparing a reaction mixture by combining the first mixture, the second mixture, and a compound that functions as a Michael catalyst; agitating the reaction mixture; wherein the active has a water solubility of at most 0.5% (w/w) at 25° C.

10 Claims, No Drawings

ENCAPSULATION METHOD

BACKGROUND

There are many applications where encapsulating an active is desirable. For example, textiles, such as wearable fabrics, are typically washed by contacting the textiles with a detergent formulation that is a combination of detergent components and other optional actives, such as bleaching agents. For ease of use, many detergent formulation users prefer an all-in-one product that incorporates the detergents and optional actives into a single product. Further, many users prefer this product to be a liquid, as compared to a solid or granular product. Water-sensitive actives are similarly useful in many other applications.

One common active is tetraacetylethylenediamine (TAED). TAED functions as a peroxy bleaching activator and a microbial control agent. TAED has been extensively used in solid detergent products. TAED, in liquid detergent formulations which contain in part water, will undergo hydrolysis and lose effectiveness as a detergent active as the TAED reacts to form N,N' diacetylethylenediamine (DAED), which is not effective as a detergent active. As such, TAED, when used without modification, is not ideal as an active for an aqueous formulation. Triacetylethylenediamine (TriAED) is another active. A method for preparing an additive containing an active that is suitable for use in formulations that contain water is desired.

SUMMARY OF THE INVENTION

A method of encapsulating an active comprising preparing a first mixture comprising the active, a compound that functions as a Michael donor, and a compound that functions as a Michael acceptor, preparing a second mixture comprising water and an emulsifier; preparing a reaction mixture by combining the first mixture, the second mixture, and a compound that functions as a Michael catalyst; agitating the reaction mixture; wherein the active has a water solubility of at most 0.5% (w/w) at 25° C.

DETAILED DESCRIPTION OF THE INVENTION

The present disclosure describes a method for preparing an additive comprising an active and the reaction product of a compound that functions as a Michael donor and a compound that functions as a Michael acceptor as part of the Michael reaction. The reaction product of a compound that functions as a Michael donor and a compound that functions as a Michael acceptor as part of the Michael reaction is referred to herein generally as a Michael product. The Michael reaction is the nucleophilic addition of a nucleophile (the compound that functions as a Michael donor) to a carbonyl compound (the compound that functions as a Michael acceptor) in the presence of a Michael catalyst.

The compound that functions as a Michael donor is selected from the group consisting of acetoacetate esters, cyanoacetate esters and malonic acid esters. In one instance, the acetoacetate ester is a mono, di, tri, or tetraacetoacetate and is preferably one of ethyl acetoacetate, 1-butylacetoacetate, methyl acetoacetate, 2-ethylhexyl acetoacetate, lauryl acetoacetate, allyl acetoacetate, 1,4-butanediol diacetoacetate, 1,6-hexanediol diacetoacetate, neopentyl glycol diacetoacetate, cyclohexane dimethanol diacetoacetate, ethoxylated bisphenol A diacetoacetate, trimethylolpropane triacetoacetate, glycerin triacetoacetate, or pentaerythritol tetraacetoacetate. In one instance, the cyanoacetate ester is a mono or bis cyanoacetate and is preferably one of ethyl cyanoacetate, butylcyanoacetate, methyl cyanoacetate, 2-ethylhexyl cyanoacetate, lauryl cyanoacetate, allyl cyanoacetate, and 1,4-butanediol bis(cyanoacetate). In one instance the malonic acid ester is one of diethyl malonate, dimethyl malonate, dibutyl malonate, bis(2-ethylhexyl) malonate, dilauryl malonate, or diallyl malonate.

The compound that functions as a Michael acceptor is a multifunctional acrylate. In one instance, the multifunctional acrylate is a diacrylate selected preferably one of 1,4-butanediol diacrylate, dipropylene glycol diacrylate, cyclohexane dimethanol diacrylate, alkoxylated hexanediol diacrylate, bisphenol A iacrylate, acrylated biphenol A diglycidylether, diethylene glycol diacrylate, ethoxylated bisphenol A diacrylate, 1,6-hexanediol diacrylate, neopentyl glycol diacrylate, polyethylene glycol diacrylate, propoxylated neopentyl glycol diacrylate, tetraethylene glycol diacrylate, triethylene glycol diacrylate, and tripropylene glycol diacrylate. In one instance, the multifunctional acrylate is a triacrylate selected preferably from one of trimethylopropane triacrylate, ethoxylated trimethylopropane triacrylate, tris(2-hydroxyethyl) isocyanurate triacrylate, propoxylated glyceryl triacrylate and pentaerythritol triacrylate. In one instance, the multifunctional acrylate is propoxylated trimethylolpropane, acrylated polyester oligomer, or acrylated urethane oligomer.

The Michael reaction is performed in a reaction mixture which includes a compound that functions as a Michael catalyst. Preferably, the Michael catalyst is an organic or an inorganic base. Examples of compounds that function as Michael catalysts include, 1,1,3,3-tetramethylguanidine, 1,8-diazabicyclo [5.4.0] undec-7-ene, NaOH, KOH, $K_2CO_3$.

The compound that functions as the Michael catalyst is preferably present in the reaction mixture at 0.1 to 10 total molar equivalents of the compound that functions as the Michael donor. The reaction mixture can be run in the presence or absence of a solvent including water, an alcohol, an ether, a hydrocarbon, or a chlorinated hydrocarbon. The temperature can range from −10° C. to 150° C. The compound that functions as the Michael donor is preferably present in a ratio the compound that functions as the Michael acceptor in the range of from 0.5:1 to 2.0:1.

The additive described herein is prepared by first providing a dispersion phase. The dispersion phase contains water and an emulsifier. In one instance, the emulsifier is a water-soluble polymer. In one instance, the emulsifier is a polyvinyl alcohol or a substituted cellulose. Examples of suitable emulsifiers include methyl cellulose, ethoxylates of fatty alcohols, sorbitan esters, polyglycerol fatty acid esters, and organic acid monoglycerides. Separately, the compound that functions as the Michael donor, the compound that functions as the Michael acceptor, and active are combined in a reaction mixture. The dispersion phase is added to the reaction mixture and is mixed to form an emulsion. The compound that functions as the Michael catalyst is then added to the emulsion with mixing until the additive is formed as beads suspended in the emulsion. The solid additive beads are isolated and formed into fine particles, such as by pushing through a sieve.

The additive is 90 weight percent or less of the active and 10 weight percent or more of the Michael product. The additive is 75 weight percent or less of the active and 25 weight percent or more the Michael product. Preferably, the additive is 50 weight percent or less of the active and 50 weight percent or more of the Michael product.

The additive described herein has a better stability in aqueous systems than the active, for example TAED, alone. For example, when the additive is detergent additive and is used in a washing machine the active is released from the copolymer, allowing the active to be available in the washing system to perform its detergent-enhancing functionality.

Additive granules can be optionally ground or milled into powder form to afford solid active ingredients which have a controlled or delayed releasing profile.

As described herein, the additive encapsulates, or partially encapsulates, the active. As used herein, "encapsulated" refers to the active being bound or retained within the Michael product network. The additives described herein are designed to release the active during a triggering event (in the context of the present disclosure, the triggering event might be use in a washing machine). When referring to the active being encapsulated, it refers to the active being retained within the Michael product network prior to the triggering event. The additives prepared according to the methods of the present disclosure have an encapsulating efficiency of 30 to 100 percent. Preferably, the additives prepared according to the methods of the present disclosure have an encapsulating efficiency of 60 to 100 percent. More preferably, the additives prepared according to the methods of the present disclosure have an encapsulating efficiency of 90 to 100 percent. As used herein, "encapsulating efficiency" refers to the percentage of prospective actives that are encapsulated in the Michael product network of the additive.

The methods described herein are suitable for preparing other types of solid powder systems. For example, the methods described herein can include but are not limited to encapsulating fabric softening agents, detergent actives, bleach actives, fertilizers, micronutrients, pesticides (fungicides, bactericides, insecticides, acaricides, nematocides, and the like), biocides, microbial control agents, polymeric lubricants, fire retardants, pigments, dyes, urea inhibitors, food additives, flavorings, pharmaceutical agents, tissues, antioxidants, cosmetic ingredients (fragrances, perfumes and the like), soil amendments (soil repelling agents, soil release agents and the like), catalysts, diagnostic agents and photoprotective agents (UV blockers and the like).

The active is selected to have a very low solubility in water in order to be compatible with the encapsulation methods described herein. Preferably, the solubility of the active in water is 1% (w/w) or less at 25° C. Preferably, the solubility of the active in water is 0.5% (w/w) or less at 25° C. As used herein, (w/w) refers to weight of active per weight of water at the specified temperature of the water.

EXAMPLES

Materials and Encapsulated Examples

Example 1

Pentaerythritol triacrylate (SR444) was obtained from Sartomer Company. TAED was obtained from Alfa Aesar. All other chemicals were obtained from Sigma-Aldrich and used as received. Deionized (DI) water was used without further purification.

TABLE 1

Formulation of Example 1

| Type of Component | Component | Formulation (g) |
|---|---|---|
| Michael Acceptor | SR444 (from Sartomer) | 13.45 |
| Michael Donor | methyl acetoacetate | 6.55 |
| Bleach active | TAED | 10.0 |
| catalyst | TMG (1,1,3,3-tetramethylguanidine) | 2.60 |
| Dispersion phase | DI Water | 19.24 |
| | 2.5% methyl cellulose solution | 3.36 |

Following the formulation listed in Table 1, the dispersion phase (DI water, methyl cellulose) was prepared in a small glass jar with agitation for 2 minutes with a stir bar.

As shown in Table 1, pre-determined amounts of Michael Donor, Michael Acceptor and TAED were added to a 100 ml 3-neck flask equipped with a stirring rod and two glass stoppers. The total amount of Michael Donor and Michael Acceptor is 20 grams, thereby the weight ratio of TAED to the combination of the Michael acceptor and Michael Donor is 1:2. The stirring rod was connected to a high speed overhead stirrer and the mixer was turned on slowly. After 2 minutes of agitation, the agitation was stopped and the dispersion phase was added to the flask. The stirrer was turned on and the rpm increased to the maximum at 2500 rpm gradually. The high speed agitation was continued for 2 minutes and then slowed to 2000 rpm for another 2 minutes. 1,1,3,3-tetramethylguanidine (TMG) was added to the stirred emulsion drop-wise. Polymer beads were obtained after 2 hours of agitation. The solid particles were isolated and washed by DI water and centrifuged. The solid particles were collected and dried in a vacuum oven at 35° C. for 2 hours. The solids were easily broken into fine particles by pushing through a 200 micron sieve.

Example 2

TABLE 2

Formulation Recipe of Example 2

| | Component | Formulation (g) |
|---|---|---|
| Michael Acceptor | SR444 | 6.31 |
| Michael Donor | methyl acetoacetate | 3.69 |
| Bleach active | TAED | 30 |
| catalyst | TMG | 1.47 |
| Dispersion phase | DI Water | 58.5 |
| | 2.5% methyl cellulose solution | 10.2 |

The procedure of Example 1 was repeated for the formulation of Example 2. The obtained solid products were easily broken into fine particles by pushing through a 500 micron sieve. The weight ratio of TAED to the combination of Michael Donor and Michael Acceptor is 3:1.

Example 3

TABLE 3

Formulation Recipe of Example 3

| | Component | Formulation (g) |
|---|---|---|
| Michael Acceptor | SR444 | 13.45 |
| Michael Donor | methyl acetoacetate | 6.55 |

TABLE 3-continued

Formulation Recipe of Example 3

| | Component | Formulation (g) |
|---|---|---|
| Bleach active | TAED | 10.0 |
| catalyst | TMG | 3.9 |
| Dispersion phase | DI Water | 19.2 |
| | 2.5% methyl cellulose solution | 3.4 |

The procedure of Example 1 was repeated for the formulation of Example 3. The obtained solid products were powder-like. The weight ratio of TAED to the combination of Michael Donor and Michael Acceptor is 1:2.

Encapsulation Performance Evaluation

Method 1: Bleaching (Oxidation) of Blue Color Food Dye 5 droplets of an aqueous blue colored food dye (FD&C blue #1, a triarylmethane dye) was added to 500 ml water and mixed for 1 hour to generate a homogenous dye/water solution. 1 gram of the dye/water solution, 1 gram $H_2O_2$ 30% water solution purchased from Sigma-Aldrich, and targeted amounts of TAED (as listed in Table 4) were added into a vial and mixed for 5 minutes as detailed in Table 4.

The loss of blue color which is indicative of bleaching (oxidation) performance was evaluated after 12 hours and compared to the control sample and the comparative sample. The control and comparative samples were prepared according to the formulation provided in Table 4 (note, the TAED provided in the Comparative sample is not encapsulated, but is provided directly to the vial; the Control sample is $H_2O_2$ in the absence of TAED).

TABLE 4

Sample Formulation of Food Color Dye Evaluation

| vial | Dye water solution (g) | 30% H2O2 (g) | TAED powder (g) | TAED examples | Observation after 12 hours |
|---|---|---|---|---|---|
| Control | 1 | 1 | 0 | No TAED | No change |
| Comparative | 1 | 1 | 0.02 | Unencapsulated TAED | Color fade |
| 1 | 1 | 1 | 0.04 | Prepared as described in Example 1 | Similar color |

As shown in Table 4, after standing at room temperature overnight (12 hours), the Comparative vial with unencapsulated TAED, has bleached the blue color (color faded). The Control vial, with hydrogen peroxide and no TAED, had no observable color change. Vial 1, having encapsulated TAED, was observed to have similar blue color after 12 hours, indicating good encapsulation efficiency.

Method 2: HPLC Analysis for Determining Hydrolysis of TAED to DAED 0.5 g of TAED without encapsulation and encapsulated TAED powders selected from the Examples listed in Tables 1, 2, and 3 were each individually added to a vial containing 20 g All™ Mighty Pac™ detergent, and shaken for 10 min. 1 droplet (ca. 0.1 g) of the mixture from each vial was added individually to separate vials containing 10 g 1:3 Acetonitrile/H2O solvent, and sonicated for 15 minutes to fully dissolve the solid TAED. The concentration of diacetylethylenediamine (DAED) of the prepared samples were measured using an Agilent 1100 High-Performance Liquid Chromatography (HPLC) with quaternary pump and diode array detector. The HPLC method conditions are summarized in Table 5.

TABLE 5

HPLC Testing Conditions

| System | Agilent 1100 with quaternary pump and diode array detector |
|---|---|
| Column | Eclipse XDB-C18: 4.6 mm × 50 mm × 5 µm |
| Column Temperature | 40° C. |
| Injection Volume | 1 µL sample |
| Flow Rate | 1 mL/min |
| Mobile Phases | A = 18.2 MΩ-cm water, B = acetonitrile |

| | Time (min) | Composition % A | % B |
|---|---|---|---|
| Gradient | 0.0 | 65 | 35 |
| | 3.5 | 0 | 100 |
| | 5.5 | 0 | 100 |
| Equilibration Time | 2.5 min | | |
| Total Run Time | ~10 | | |
| Detection | UV (DAD) @ 216 nm, BW 4 nm, 1 cm cell (TAED) | | |
| | UV (DAD) @ 205 nm, BW 4 nm, 1 cm cell (DAED) | | |

TABLE 6

HPLC Evaluation Results on DAED concentration (%)

| | Initial Day | Day 2 | Day 7 | Day 20 | Day 36 |
|---|---|---|---|---|---|
| Unencapsulated TAED | 0.0000 | 0.1162 | 0.2845 | 0.5928 | 0.7602 |
| Example 1 | 0.0000 | 0.0000 | 0.0345 | 0.0753 | 0.0594 |
| Example 2 | 0.0000 | 0.0488 | 0.1247 | 0.2072 | 0.2670 |
| Example 3 | 0.0000 | 0.0427 | 0.1125 | 0.1810 | 0.2274 |

As shown in Table 6, for TAED without any encapsulation. The DAED concentration is increasing dramatically, which for other examples, the DAED increased slowly. As DAED was generated from TAED degradation, the slow releasing profile of DAED indicates good encapsulation efficiency and effective protection by the encapsulation shell.

The invention claimed is:

1. A method of encapsulating an active comprising:
    preparing a first mixture comprising the active, a compound that functions as a Michael donor, and a compound that functions as a Michael acceptor;
    preparing a second mixture comprising water and an emulsifier;
    preparing a reaction mixture by combining the first mixture, the second mixture, and a compound that functions as a Michael catalyst;
    agitating the reaction mixture; wherein
    the active has a water solubility of at most 0.5% (w/w) at 25° C.;
    wherein the compound that functions as the Michael donor is selected from the group consisting of acetoacetate esters, cyanoacetate esters and malonic acid esters; and
    wherein the compound that functions as the Michael acceptor is a multifunctional acrylate and is:
    a diacrylate selected from the group consisting of 1,4-butanediol diacrylate, dipropylene glycol diacrylate, cyclohexane dimethanol diacrylate, alkoxylated hexanediol diacrylate, bisphenol A diacrylate, acrylated bisphenol A diglycidylether, diethylene glycol diacrylate, ethoxylated bisphenol A diacrylate, 1,6-hexanediol diacrylate, neopentyl glycol diacrylate, polyethylene glycol diacrylate, propoxylated neopentyl glycol diacrylate, tetraethylene glycol diacrylate, triethylene glycol diacrylate, and tripropylene glycol diacrylate; or a triacrylate selected from the group consisting of trimethylopropane triacrylate, ethoxylated trimethylopropane triacrylate, tris(2-hydroxyethyl) isocyanurate triacrylate, propoxylated glyceryl triacrylate and pentaerythritol triacrylate; or acrylated polyester oligomer; or an acrylated urethane oligomer.

2. The method of claim 1, wherein the compound that functions as the Michael donor is an acetoacetate ester, and the acetoacetate ester is a mono, di, tri, or tetraacetoacetate selected from the group consisting of ethyl acetoacetate, 1-butylacetoacetate, methyl acetoacetate, 2-ethylhexyl acetoacetate, lauryl acetoacetate, allyl acetoacetate, 1,4-butanediol diacetoacetate, 1,6-hexanediol diacetoacetate, neopentyl glycol diacetoacetate, cyclohexane dimethanol diacetoacetate, ethoxylated bisphenol A diacetoacetate, trimethylolpropane triacetoacetate, glycerin triacetoacetate, and pentaerythritol tetraacetoacetate.

3. The method of claim 1, wherein the compound that functions as the Michael donor is an cyanoacetate ester, and the cyanoacetate ester is a mono or bis cyanoacetate selected from the group consisting of ethyl cyanoacetate, butylcyanoacetate, methyl cyanoacetate, 2-ethylhexyl cyanoacetate, lauryl cyanoacetate, allyl cyanoacetate, and 1,4-butanediol bis(cyanoacetate).

4. The method of claim 1, wherein the compound that functions as the Michael donor is a malonic acid ester, and the malonic acid ester is selected from the group consisting of diethyl malonate, dimethyl malonate, dibutyl malonate, bis(2-ethylhexyl) malonate, dilauryl malonate, and diallyl malonate.

5. The method of claim 1, wherein the compound that functions as the Michael catalyst is an organic or inorganic base.

6. The method of claim 5, wherein the compound that functions as the Michael catalyst is selected from the group consisting of 1,1,3,3-tetramethylguanidine, 1,8-diazabicyclo[5.4.0] undec-7-ene, NaOH, KOH, $K_2CO_3$.

7. The method of claim 1, wherein the active is selected from the group consisting of fabric softening agents, detergents, bleach actives, fertilizers, micronutrients, pesticides, fungicides, bactericides, insecticides, acaricides, nematocides, biocides, microbial control agents, polymeric lubricants, fire retardants, pigments, dyes, urea inhibitors, food additives, flavorings, pharmaceutical agents, tissues, antioxidants, fragrances, soil amendments, catalysts, diagnostic agents and photoprotective agents.

8. The method of claim 7, wherein the active comprises one or both of tetraacetylethylenediamine and triacetylethylenediamine.

9. The method of claim 1, wherein the emulsifier is a water-soluble polymer.

10. The method of claim 1, wherein the emulsifier is a polyvinyl alcohol or a substituted cellulose.

\* \* \* \* \*